(12) United States Patent
Kang et al.

(10) Patent No.: US 7,817,775 B2
(45) Date of Patent: Oct. 19, 2010

(54) RADIATION INSPECTION SYSTEM

(75) Inventors: Kejun Kang, Beijing (CN); Haifeng Hu, Beijing (CN); Zhiqiang Chen, Beijing (CN); Shangmin Sun, Beijing (CN); Guang Yang, Beijing (CN); Fengjun Zhang, Beijing (CN); Yong Bi, Beijing (CN); Yucheng Wu, Beijing (CN); Jianjun Li, Beijing (CN); Rongxuan Liu, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 346 days.

(21) Appl. No.: 11/997,448

(22) PCT Filed: Jan. 8, 2007

(86) PCT No.: PCT/CN2007/000066

§ 371 (c)(1), (2), (4) Date: Jan. 31, 2008

(87) PCT Pub. No.: WO2007/079675

PCT Pub. Date: Jul. 19, 2007

(65) Prior Publication Data

US 2008/0197279 A1    Aug. 21, 2008

(30) Foreign Application Priority Data

Jan. 11, 2006    (CN) .......................... 2006 1 0011148

(51) Int. Cl.
*G01N 23/04*    (2006.01)

(52) U.S. Cl. ........................................ 378/57; 378/208

(58) Field of Classification Search .................... 378/57, 378/209, 208, 210
See application file for complete search history.

(56) References Cited

U.S. PATENT DOCUMENTS

2002/0148928 A1*   10/2002   Oki .......................... 244/118.1

(Continued)

FOREIGN PATENT DOCUMENTS

CN           2233005 Y         8/1996

(Continued)

OTHER PUBLICATIONS

International Search Report for PCT/CN2007/000066; Form PCT/ISA/210 (second sheet) (Apr. 2005), 4 pages.

(Continued)

*Primary Examiner*—Hoon Song
(74) *Attorney, Agent, or Firm*—Westman, Champlin & Kelly, P.A.

(57) ABSTRACT

Disclosed is an inspection system for inspecting a cargo by using radiation, comprising: a main plate conveyor; a radiation scanning unit that spans said main plate conveyor and is provided above said main plate conveyor, for scanning the cargo provided on the main plate conveyor; auxiliary conveyors that are provided at the front end and rear end of said main plate conveyor, respectively, so as to load the cargo to be inspected onto said main plate conveyor and to unload the inspected cargo from said main plate conveyor; and lifting devices for lifting said auxiliary conveyors. The inspection system according to the present invention occupies less area, has simple corollary equipments, a lower operating cost, and excellent compatibility, and can be widely applied.

14 Claims, 3 Drawing Sheets

U.S. PATENT DOCUMENTS

2004/0213374 A1* 10/2004 Kang et al. .................. 378/57

FOREIGN PATENT DOCUMENTS

| | | |
|---|---|---|
| CN | 2353720 Y | 12/1999 |
| CN | 2393095 Y | 8/2000 |
| CN | 1392404 | 1/2003 |
| CN | 1405555 | 3/2003 |
| CN | 2575084 Y | 9/2003 |
| CN | 2632671 Y | 8/2004 |
| CN | 2670336 Y | 1/2005 |
| CN | 2711728 Y | 7/2005 |
| DE | 09117188 U1 | 11/1991 |
| JP | 8333094 | 12/1996 |
| JP | 2006307354 | 11/2006 |
| WO | WO 2004/010127 | 1/2004 |

OTHER PUBLICATIONS

Written Opinion for PCT/CN2007/000066; Jan. 11, 2006; PCT/ISA/237/ . . . (2005 ..4 ..), 4 pages.

* cited by examiner

US 7,817,775 B2

RADIATION INSPECTION SYSTEM

CROSS-REFERENCE TO RELATED APPLICATION

This Application is a Section 371 National Stage Application of International Application No. PCT/CN2007/000066, filed Jan. 8, 2007, published as WO 2007/079675, not in English, the content of which is hereby incorporated by reference in its entirety.

FIELD OF THE INVENTION

The present invention generally relates to an inspection system for inspecting cargo by means of radiation (rays). In particular, the present invention relates to an X-ray inspection system adapted to inspect pallet cargo, air containerized cargo or other larger cargo.

BACKGROUND OF THE INVENTION

A large-scale air containerized cargo inspection system is an inspection system urgently required by air customs. Currently, larger air cargo is inspected by opening a cargo container containing the larger air cargo or by using an X-ray machine.

However, the inspection operation of opening the cargo container is time-consuming and has a low efficiency and a high inspection cost. The inspection using the X-ray machine is implemented by reflecting the cargo to form an image. However, since the rays from the X-ray machine has low energy and poor penetrability, and only the portion of the cargo that is within a certain extent close to the ray source can be clearly imaged, and image quality and range of application of the machine can not meet requirement.

Accordingly, a cargo inspection system is disclosed in CN1405555A, entitled as "air containerized cargo/pallet cargo inspection system", filed by the applicant of the present application. The cargo inspection system comprises an inverted-U shaped scanning frame composed of a radiation source, a detector array, a collimator, a subtense device arm, and an upright detector arm; a combined transporting system composed of a main plate conveyor and an auxiliary roller conveyor; a radiation shielding system, a device compartment, an operation room, and so on.

During loading the air containerized cargo/pallet cargo, when the bottom surface of the air containerized cargo/pallet cargo is brought into contact with the rollers provided on the outermost side of the loading roll table, the auxiliary roller conveyor is actuated, and then the rollers carry and transport the cargo onto the main plate conveyor. The main plate conveyor carries the cargo to pass through the region under the scanning frame.

However, in the above conventional inspection system, the heights of the auxiliary roller conveyor and the main plate conveyor are constant. Thus, an additional transport trailer, such as a fork truck or a full trailer, must be employed to transport the cargo between a truck and the auxiliary roller conveyor before and after the cargo is inspected. Therefore, when the above conventional inspection system is installed, a space for running and steering the transport trailer should be provided at the two ends of the system, and thus a larger installation area is required.

Therefore, the above conventional radiation inspection system has the following technical problems. The system occupies a larger region, the corollary equipments for it are complicated, and has a poor compatibility and a higher operation cost, and is not adapted for a freight yard with a limited space.

SUMMARY OF THE INVENTION

The embodiment of the present invention provides an inspection system for inspecting a cargo that occupies less area without requiring a transport trailer, has excellent compatibility and lower operating cost, and can be widely applied, or that has at least one of the above-mentioned advantages.

Accordingly, according to one aspect of the present invention, an inspection system for inspecting a cargo by using radiation, comprising: a main plate conveyor; a radiation scanning unit that spans said main plate conveyor and is provided above said main plate conveyor, for scanning the cargo provided on the main plate conveyor; auxiliary conveyors that are provided at a front end and a rear end of said main plate conveyor, respectively, so as to load the cargo to be inspected onto said main plate conveyor and to unload the inspected cargo from said main plate conveyor; and lifting devices for lifting said auxiliary conveyors.

Preferably, said auxiliary conveyors are roller conveyors.

Further, each of said lifting devices comprises: an upper platform that supports said roller conveyor on an upper surface of the upper platform and is provided along a longitudinal direction thereof with an upper sliding groove; a low platform that is provided along the longitudinal direction thereof with a lower sliding groove corresponding to the upper sliding groove; a link mechanism including a first link and a second link, in which said first link and said second link are pivotally connected with each other at respective substantial centers in longitudinal directions thereof, and an upper end of the first link and a low end of the second link are pivotally connected to the upper platform and the low platform, respectively, and a low end of the first link and an upper end of the second link are slidably engaged in said low sliding groove and said upper sliding groove, respectively; and an actuator for driving said first link and said second link to pivot with respect to each other, so that the upper platform is lifted and lowered.

Further, guiding wheels are provided at the low end of the first link and at the upper end of the second link, respectively, and the guiding wheels are slidably engaged in the upper sliding groove and the low sliding groove.

Further, said upper sliding groove is formed on a longitudinal side face of the upper platform, and said low sliding groove is formed on a longitudinal side face of the low platform which is on the same side as the longitudinal side face of the upper platform, and the upper end of the first link and the low end of the second link are hinged to the longitudinal side faces of the upper platform and the low platform, respectively.

Preferably, one end of said actuator is pivotally connected near the low end of the second link, and the other end thereof is pivotally connected between the upper end of the first link and the longitudinal center of the first link.

Further, said actuator comprises a hydraulic cylinder or an air cylinder. Alternatively, said actuator comprises: a lead screw; a threaded sleeve that is engaged with the lead screw, so that the threaded sleeve can longitudinally move with respect to the lead screw by rotation of the lead screw; and a motor for driving the lead screw to rotate. Further, said actuator comprises a telescopic bar.

Preferably, said radiation scanning unit comprises: a radiation source that is provided at a first side of the maim plate conveyor and emits rays; a collimator that is provided between the radiation source and the first side of the main plate conveyor and is adapted to collimate the rays emitted from the radiation source; an upright arm frame that is provided at a second side of said main plate conveyor opposite to the first side of the main plate conveyor, and is provided with a first detector array that receives the rays emitted from the radiation source and collimated by the collimator, and a horizontal or transverse arm frame, one end of which is connected with an upper end of the upright arm frame, and the other end of which spans said main plate conveyor so as to be connected with the collimator, so that the upright arm frame, the horizontal arm frame, and the collimator constitute an inverted-U shaped frame, and the horizontal arm frame is provided with a second detector array that receives the rays emitted from the radiation source and collimated by the collimator.

Furthermore, the inspection system according to the present invention further comprises a radiation shielding wall that is provided on an outside of the inverted-U shaped frame at the second side of the main plate conveyor to shield the rays.

Further, protection frames may be provided at the ends of said auxiliary conveyors apart from said main plate conveyor, respectively.

Preferably, the inspection system according to the present invention further comprises traction devices that are provided on ends of said upper platforms close to said main plate conveyor, respectively, each of the traction devices comprises: a drum; a motor for driving the drum to rotate; and a traction rope, one end of which is wound on said drum, and the other end of which drags the cargo to be inspected, so that the cargo is dragged onto the auxiliary conveyors.

According to the embodiment of the present invention, said radiation source may be an X-ray tube or an isotope radiation source.

Alternatively, each of said lifting devices comprises: a platform for supporting said auxiliary conveyor; and a hydraulic cylinder provided under the platform and used to support and lift said platform.

Alternatively, each of said lifting devices comprises: a platform for supporting said auxiliary conveyor; and a leading screw transmission device, comprising a leading screw, a motor for driving the leading screw, and a nut engaged with the leading screw and fixed to the bottom surface of said platform, so that said nut moves along the leading screw, thereby lifting said platform and said auxiliary conveyor, when the motor is actuated to drive the leading screw to rotate.

In accordance with the embodiment of the present invention, since the auxiliary conveyors capable of being lifted are employed, no transport trailer is needed. Furthermore, the inspection system has advantages that it occupies less region, has lower operating cost and excellent compatibility, and can be widely applied, and is adapted to inspect air containerized cargo, pallet cargo, or other cargo transported through road, train, seaport, and so on, which is inspected without opening cargo containers

BRIEF DESCRIPTION OF THE DRAWING

These and/or other aspects and advantages of the present invention will be more readily apparent from the following detailed description of preferred embodiments when taken together with the accompanying drawings.

DETAILED DESCRIPTION OF THE PREFERRED EMBODIMENTS

Figure 1:
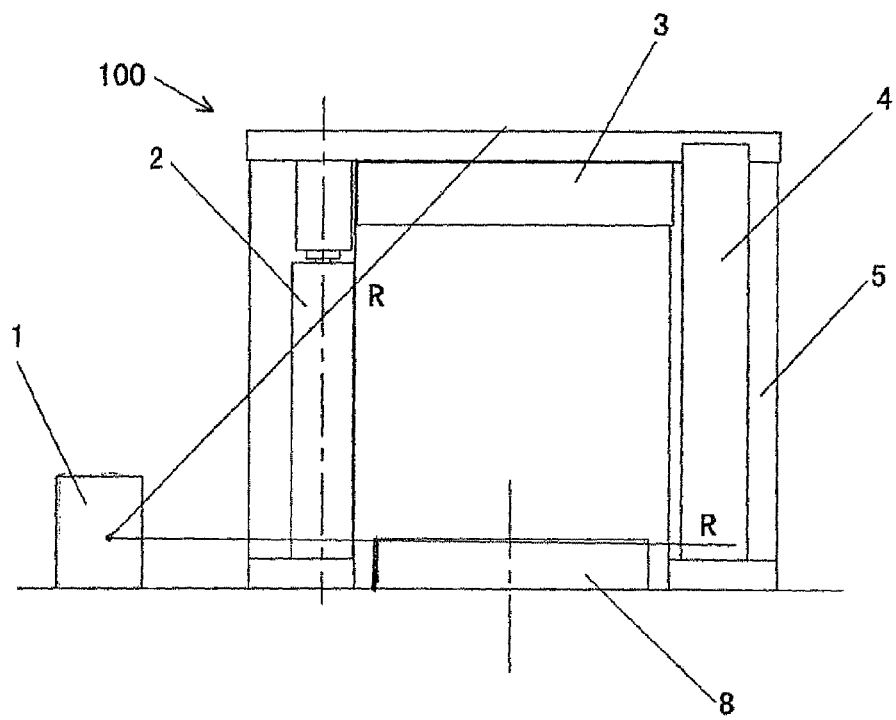
FIG. 1 is a schematic diagram of a radiation inspection system according to an embodiment of the present invention, mainly showing a radiation scanning unit of the radiation inspection system.

Reference will now be made in detail to the embodiment of the present invention, examples of which are illustrated in the accompanying drawings, wherein like reference numerals refer to the like elements throughout. The embodiments are described below to explain the present invention by referring to the figures.

Referring to FIG. 1 to FIG. 4, an inspection system 100 according to the present invention, that inspects air containerized cargo, pallet cargo, and other larger cargo by using radiation of, for example, X rays, comprises a main plate conveyor 8, a radiation scanning unit, auxiliary conveyors 7, and lifting devices 10.

Specifically, as shown in FIG. 1, the radiation scanning unit spans above the main plate conveyor 8 to scan a cargo provided on the main plate conveyor 8. For instance, the main plate conveyor 8 carries and moves the cargo along the direction D indicated by an arrow in FIG. 4 to pass through the radiation scanning unit so as to scan and image the cargo, thereby implementing inspection. Alternatively, the main plate conveyor 8 can carry and move the cargo along an opposite direction to the direction D to pass through the radiation scanning unit, or reciprocate the cargo along the direction D and the opposite direction thereto to pass through the radiation scanning unit, so that the cargo is repeatedly inspected.

Figure 2:
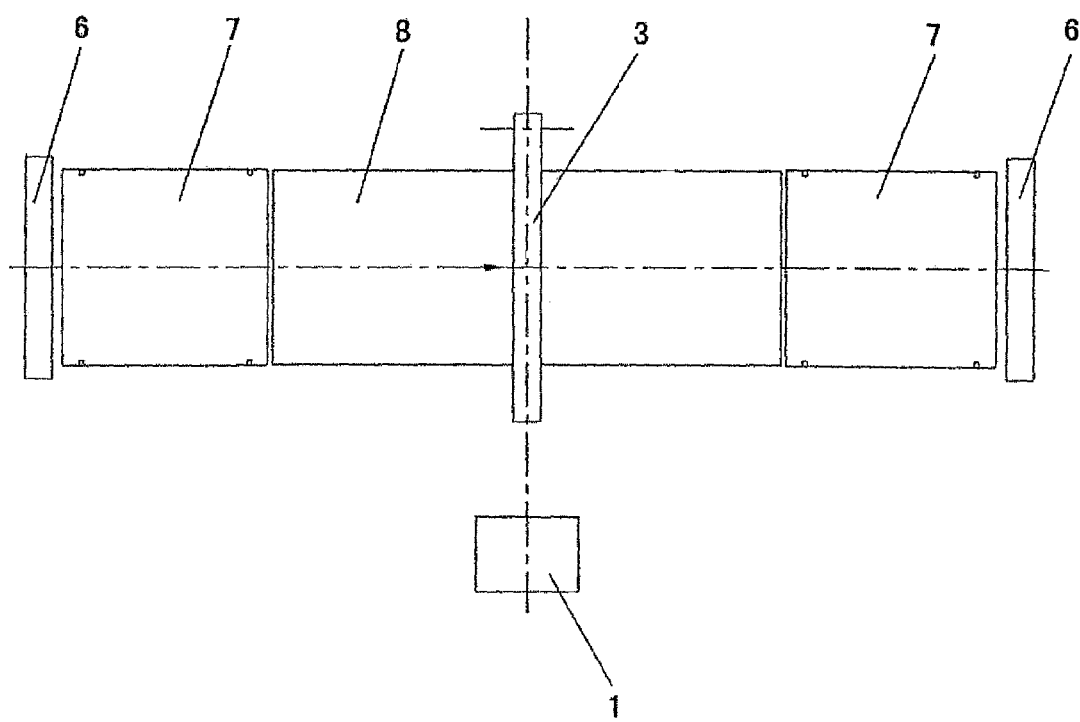
FIG. 2 is a top view of the radiation inspection system shown in FIG. 1, in which the radiation inspection system is rotated by 90 degrees.
Figure 3:
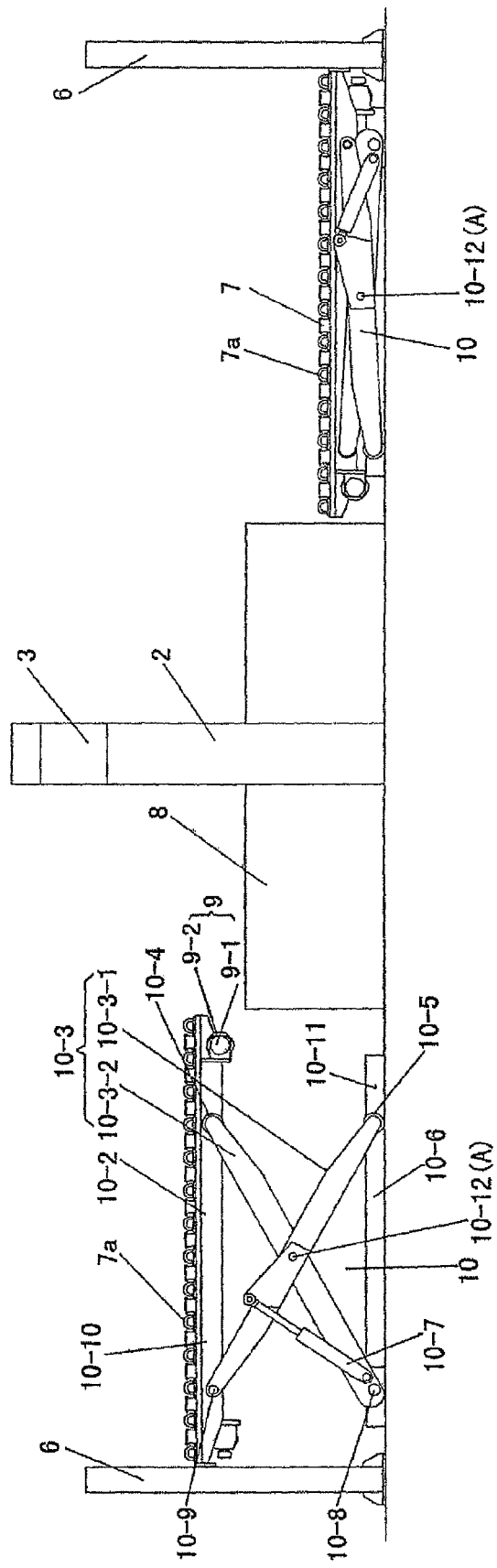
FIG. 3 is a schematic diagram of the radiation inspection system according to the embodiment of the present invention, mainly showing a roller conveyor and a lifting device thereof.
Figure 4:
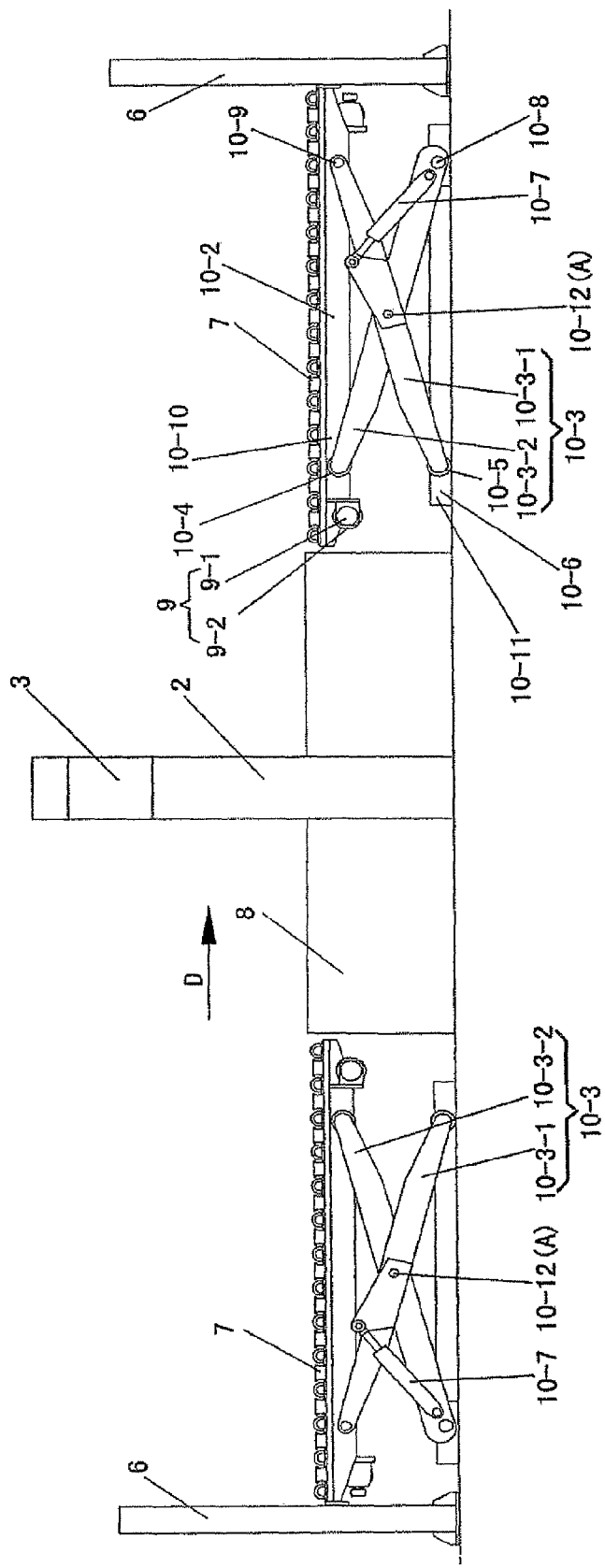
FIG. 4 is a schematic diagram of the radiation inspection system according to the embodiment of the present invention, in which the radiation inspection system is in an inspecting state.

As shown in FIGS. 2-4, the auxiliary conveyors 7 are provided in front of (the left side in FIGS. 2-4) and behind (the right side in FIGS. 2-4) the main plate conveyor 8, respectively, to load the cargo to be inspected onto the main plate conveyor 8 and to unload the inspected cargo from the main plate conveyor 8.

In the embodiment of the present invention, as shown in FIGS. 2-4, for the propose of facilitating description, the auxiliary conveyor provided at the left side of the main plate conveyor 8 is referred to as an auxiliary loading conveyor for loading the cargo onto the main plate conveyor 8; and the auxiliary conveyor provided at the right side of the main plate conveyor 8 is referred to as an auxiliary unloading conveyor for unloading the cargo from the main plate conveyor 8. However, since the main plate conveyor 8 can carry the cargo provided thereon to reciprocatively pass through the radiation scanning unit so as to repeatedly inspect the cargo, the terminologies "loading" and "unloading" are only illustrative, and are not for limiting the present invention. Alternatively, for example, in FIGS. 2-4, the auxiliary conveyor provided at the left side of the main plate conveyor 8 is used to unload the cargo from the main plate conveyor 8, and the auxiliary conveyor provided at the right side of the main plate conveyor 8 is used to load the cargo onto the main plate conveyor 8.

More specifically, as shown FIGS. 3 and 4, the auxiliary conveyors are roller conveyors. However, the auxiliary conveyors 7 are not limited to roller conveyors, and can be, for example, plate conveyors or any other suitable conveyors.

The lifting devices 10 are used for lifting the auxiliary conveyors 7, respectively, so that a height of the auxiliary conveyors 7 can be adjusted to be in the same level as that of the main plate conveyor 8 so as to load the cargo onto the main plate conveyor 8 from the auxiliary conveyors 7 or unload the cargo to the auxiliary conveyors 7 from the main plate conveyor 8, or the height of the auxiliary conveyors 7 can be adjusted to be lower or higher than that of the main plate conveyor 8. It should be noted that the height of the auxiliary conveyors provided at the two sides of the main plate conveyor 8 are separately adjusted.

Specifically, shown in FIGS. 3 and 4, each of the lifting devices 10 comprises an upper platform 10-2, a low platform 10-6, a link mechanism 10-3, and an actuator 10-7.

The upper platform 10-2 is used for supporting the auxiliary roller conveyor 7 on an upper surface thereof and is provided along a longitudinal direction thereof with an upper sliding groove 10-10. More specifically, rollers 7a and other component parts of the auxiliary conveyor 7 are provided on the upper platform 10-2. The low platform 10-6 is provided along a longitudinal direction thereof with a low sliding groove 10-11 corresponding to the upper sliding groove 10-10.

The link mechanism 10-3 comprises a first link 10-3-1 and a second link 10-3-2. The first link 10-3-1 and the second link 10-3-2 are pivotally connected with each other at substantial centers A along longitudinal directions thereof via, for example, a pin 10-12. An upper end of the first link 10-3-1 (i.e., the end apart from the main plate conveyor 8) is pivotally connected to the upper platform 10-2 via, for example, a pin 10-9, and a low end of the second link 10-3-2 (i.e., the end apart from the main plate conveyor 8) is pivotally connected (hinged, in this embodiment,) to the low platform 10-6 via, for example, a pin 10-8, while a low end of the first link 10-3-1 (i.e., the end close to the main plate conveyor 8) and an upper end of the second link 10-3-2 (i.e., the end close to the main plate conveyor 8) are slidably engaged in the low sliding groove 10-10 and the upper sliding groove 10-11, respectively.

Preferably, guiding wheels 10-4 and 10-5 are provided at the low end of the first link 10-3-1 and at the upper end of the second link 10-3-2, respectively. The guiding wheels 10-4 and 10-5 are engaged into the upper sliding groove 10-10 and the low sliding groove 10-11, so that the low end of the first link 10-3-1 and the upper end of the second link 10-3-2 can slide within the upper sliding groove 10-10 and the low sliding groove 10-1.

More specifically, the upper sliding groove 10-10 is formed on a first side face of the upper platform 10-2 (i.e., the low side face shown in FIG. 2), and the low sliding groove 10-11 is formed on a first side face of the low platform 10-6 (i.e., the low side face shown in FIG. 2). Meanwhile, the upper end of the first link 10-3-1 and the low end of the second link 10-3-2 are pivotally hinged to the firs side faces of the upper platform 10-2 and the low platform 10-6 via the pins 10-9 and 10-8, respectively. However, one skilled in the art can understand that the formation positions of the upper sliding groove and the low sliding groove are not limited to be on the side faces of the upper platform and the low platform, and the upper sliding groove and the low sliding groove can be formed, for example, lower surfaces of the upper platform and the low platform, respectively. Furthermore, a number of the sliding grooves may be any appropriate number.

It should be noted that the lifting devices for lifting the auxiliary conveyors 7 are not limited to the above-mentioned embodiment, and one skilled in the art can achieve lifting of the auxiliary conveyors in any suitable way. For instance, the upper platform 10-2 can be supported by a hydraulic cylinder or a lead screw, and be lifted by actuating the hydraulic cylinder or driving the lead screw to rotate, so that the auxiliary conveyors 7 can be lifted.

The actuator 10-7 drives the first link 10-3-1 and the second link 10-3-2 to rotate about the pin 10-12 with respect to each other, so that the upper platform 10-2 is lifted and lowered with respect to the low platform 10-6.

Specifically, as shown in FIG. 3 and FIG. 4, one end of the actuator 10-7 (the low end in FIG. 3) is pivotally connected near the low end of the second link 10-3-2, and the other end thereof is pivotally connected between the upper end of the first link 10-3-1 and the longitudinal center A of the first link.

As shown in the left part of FIG. 3, when the cylinder bar of the hydraulic cylinder is extended out, the first link 10-3-1 and the second link 10-3-2 are pivoted about the pin 10-12 with respect to each other, so that a distance between the upper end of the first link 10-3-1 and the low end of the second link 10-3-2 and a distance between the low end of the first link 10-3-1 and the upper end of the second link 10-3-2 are increased, and at the same time the low end of the first link 10-3-1 and the upper end of the second link 10-3-2 slide within the low sliding groove 10-11 and the upper sliding groove 10-10 to leave apart from the main plate conveyor 8, so that the upper platform 10-2 is lifted with respect to the low platform 10-6.

In contrast, as shown in the right part of FIG. 3, when the cylinder bar of the hydraulic cylinder is drawn back, the upper platform 10-2 is lowered with respect to the low platform 10-6. Thus, a height of the auxiliary conveyors 7 can be adjusted to be in the same level as that of the main plate conveyor 8 (as shown in FIG. 4), or be lower or higher than that of the main plate conveyor 8 (as shown in FIG. 3).

In the embodiment shown in FIGS. 3 and 4, the actuator 10-7 is a hydraulic cylinder or an air cylinder, but is not limited to this. The actuator 10-7 may be a telescopic bar. Alternatively, the actuator 10-7 comprises a lead screw; a threaded sleeve that is engaged with the lead screw, so that the threaded sleeve can longitudinally move with respect to the lead screw by rotation of the lead screw; and a motor for driving the lead screw to rotate. In this case, the operation of the actuator 10-7 is similar to that of the above-mentioned hydraulic cylinder or air cylinder, and the detailed description for it is omitted.

The lifting device for lifting the auxiliary conveyor 7 is not limited to the above-mentioned link mechanism. Alternatively, the lifting device may comprise a platform (no shown), similar to the upper platform 10-2, for supporting the auxiliary conveyor 7, and a hydraulic cylinder provided under the platform and used to support and lift the platform. A number of the hydraulic cylinders may be determined according to practical requirement. Furthermore, instead of the above-mentioned hydraulic cylinder, a leading screw transmission device can be used. The leading screw transmission device may comprises a leading screw, a motor for driving the leading screw, and a nut engaged with the leading screw and fixed to a bottom surface of the platform for supporting the auxiliary conveyor 7. When the motor is actuated, the leading screw is rotated, so that the nut moves along the leading screw, thereby driving the platform and the auxiliary conveyor 7 to lift. The above contents can be easily understood by one skilled in the art, and accordingly, the detailed description thereof is omitted.

In accordance with the embodiment of the present invention, as shown in FIG. 1 and FIG. 2, the radiation scanning unit comprises a radiation source 1, such as an X-ray tube and an isotope radiation source, a collimator 2, an upright arm frame 4, and a horizontal or transverse arm frame 3. Preferably, the radiation scanning unit further comprises a radiation shielding wall 5.

Specifically, the radiation source 1 is provided at a first side of the main plate conveyor 8 (the left side in FIG. 1, i.e., the low side in FIG. 2) and emits rays R. It should be noted that although two straight lines are used to indicate rays R in FIG. 1, a ray beam emitted from the radiation source 1 is collimated by the collimator 2 to form a sector-shaped ray beam plane.

The collimator 2 is provided between the radiation source 1 and the first side of the main plate conveyor 8 and is adapted to collimate the rays R emitted from the radiation source 1.

The upright arm frame 4 is provided at a second side of the main plate conveyor 8 (the left side in FIG. 1, i.e., the upper side in FIG. 2) opposite to the first side of the main plate conveyor 8, and the upright arm frame is provided with a first detector array (not shown) that receives the rays R emitted from the radiation source 1 and collimated by the collimator 2.

One end of the horizontal arm frame 3 (the right end in FIG. 1) is connected with an upper end of the upright arm frame 4, and the other end thereof spans the main plate conveyor 8 so as to be connected with the collimator 2, that is, the collimator 2 is supported on the other end of the horizontal arm frame 3, so that the upright arm frame 4, the horizontal arm frame 3, and the collimator 2 constitute an inverted-U shaped frame. The horizontal arm frame 3 is provided with a second detector array (not shown) that receives the rays R emitted from the radiation source 1 and collimated by the collimator 2.

The radiation shielding wall 5 is provided at the second side of the main plate conveyor 8 and on an outside of the inverted-U shaped frame to shield the rays R (including rays generated due to diffusing, refracting and the like).

Alternatively, the inspection system 100 according to the embodiment of the present invention further comprises protection frames 6 that are provided at ends of the auxiliary conveyors 7 apart from the main plate conveyor 8, respectively, so that the cargo is prevented from dropping from the auxiliary conveyors 7.

Alternatively, the inspection system 100 according to the embodiment of the present invention further comprises traction devices 9 that are provided on ends of the upper platform 2 close to the main plate conveyor 8, respectively, for dragging (loading) the cargo onto the auxiliary conveyors 7.

Specifically, each of the traction devices 9 comprises a drum 9-1, a motor (not shown) for driving the drum 9-1 to rotate, and a traction rope 9-2. One end of the traction rope 9-2 is wound on the drum 9-1, and the other end thereof drags the cargo to be inspected, so that the cargo is dragged onto the auxiliary convey or is dragged down from the auxiliary conveyor.

It should be noted that the inspection system according to the present invention further comprises a scan controlling module, an image capturing module, an operation inspecting device, a data processing unit, and a controlling unit. These component parts are similar to those in the prior art, and the detailed description thereof is omitted.

Next, the operation of inspecting the cargo using the radiation inspection system in accordance with the embodiment of the present invention will be explained.

(1) Firstly, the inspection system is started up for warming up and then becomes in a standby condition.

(2) The auxiliary loading roller conveyor 7 (for example, the auxiliary conveyor 7 at the left side in FIGS. 2-4) is adjusted to an appropriate height by the lifting device 10, so that the cargo can be loaded onto the auxiliary conveyor 7.

(3) The containerized cargo is dragged onto the auxiliary loading roller conveyor 7 by the traction device 9 or by manual work.

(4) The auxiliary loading roller conveyor 7 is adjusted to flush with the main plate conveyor 8, as shown in FIG. 4.

(5) The auxiliary loading roller conveyor 7 is stated up to transport the cargo onto the main plate conveyor 8, and then the main plate conveyor 8 carries the cargo provided thereon to move along the direction D to pass through the radiation scanning unit; when the cargo passes through a ray beam plane, scanning data is generated and transmitted to the data processing center to form a real-time cargo image.

(6) When the cargo has passed through the ray beam plane, displaying the image is stopped; and the inspected cargo is transported to the auxiliary unloading roller conveyor 7 (the auxiliary conveyor at the right side in FIGS. 2-4) from the main plate conveyor 8, and at this point, the height of the auxiliary unloading roller conveyor 7 is the same as that of the main plate conveyor 8.

(7) The height of the auxiliary unloading roller conveyor 7 is adjusted to be in an appropriate level, and then the cargo is removed.

If the inspector judges by observing the cargo image that the cargo should be re-inspected, the cargo on the auxiliary unloading roller conveyor 7 is transported onto the main plate conveyor 8 by the controlling unit, and then the main plate conveyor 8 carries the cargo to move along the opposite direction to the direction D to pass through the radiation scanning unit, so that the cargo is re-inspected, or the cargo can be unloaded, and then the cargo container is opened so as to re-inspect the cargo. Also, the cargo can be repeatedly inspected by changing arrangement or angle of the cargo, so that accuracy of inspection is improved, as shown FIG. 4.

Although an embodiment of the present invention has been shown and described, it would be appreciated by those skilled in the art that changes may be made in this embodiment without departing from the principles and spirit of the invention, the scope of which is defined in the claims and their equivalents.

What is claimed is:

1. An inspection system for inspecting a cargo by using radiation, comprising:

a main plate conveyor;

a radiation scanning unit that spans said main plate conveyor and is provided above said main plate conveyor, for scanning the cargo provided on the main plate conveyor;

auxiliary conveyors that are provided at a front end and a rear end of said main plate conveyor, respectively, so as to load the cargo to be inspected onto said main plate conveyor and to unload the inspected cargo from said main plate conveyor; and lifting devices for lifting said auxiliary conveyors, each comprising an upper platform for supporting said auxiliary conveyor; and traction devices that are provided on ends of said upper platforms close to said main plate conveyor, respectively, each of the traction devices comprises:

a drum;

a motor for driving the drum to rotate; and a traction rope, one end of which is wound on said drum, and the other end of which drags the cargo to be inspected, so that the cargo is dragged onto the auxiliary conveyors or is dragged down from the auxiliary conveyors.

2. The inspection system according to claim 1, wherein said auxiliary conveyors are roller conveyors.

3. The inspection system according to claim 2, wherein the upper platform supports said roller conveyor on an upper surface thereof and is provided along a longitudinal direction thereof with an upper sliding groove;
wherein each of said lifting devices further comprises:
a low platform that is provided along a longitudinal direction thereof with a lower sliding groove corresponding to the upper sliding groove;
a link mechanism including a first link and a second link, in which said first link and said second link are pivotally connected with each other at respective substantial centers along longitudinal directions thereof, and an upper end of the first link and a low end of the second link are pivotally connected to the upper platform and the low platform, respectively, and a low end of the first link and an upper end of the second link are slidably engaged in said low sliding groove and said upper sliding groove, respectively; and
an actuator for driving said first link and said second link to pivot with respect to each other, so that the upper platform is lifted and lowered.

4. The inspection system according to claim 3, wherein guiding wheels are provided at the low end of the first link and at the upper end of the second link, respectively, and the guiding wheels are slidably engaged in the upper sliding groove and the low sliding groove.

5. The inspection system according to claim 4, wherein said upper sliding groove is formed on a longitudinal side face of the upper platform, and said low sliding groove is formed on a longitudinal side face of the low platform which is on the same side as the longitudinal side face of the upper platform, and
the upper end of the first link and the low end of the second link are hinged to the longitudinal side faces of the upper platform and the low platform, respectively.

6. The inspection system according to claim 5, wherein one end of said actuator is pivotally connected near the low end of the second link, and the other end thereof is pivotally connected between the upper end of the first link and the longitudinal center of the first link.

7. The inspection system according to claim 6, wherein said actuator comprises a hydraulic cylinder or an air cylinder.

8. The inspection system according to claim 6, wherein said actuator comprises:
a lead screw;
a threaded sleeve that is engaged with the lead screw, so that the threaded sleeve can longitudinally move with respect to the lead screw by rotation of the lead screw; and
a motor for driving the lead screw to rotate.

9. The inspection system according to claim 6, wherein said actuator comprises a telescopic bar.

10. The inspection system according to claim 1, wherein said radiation scanning unit comprises:
a radiation source that is provided at a first side of the maim plate conveyor and emits rays;
a collimator that is provided between the radiation source and the first side of the main plate conveyor and is adapted to collimate the rays emitted from the radiation source;
an upright arm frame that is provided at a second side of said main plate conveyor opposite to the first side of the main plate conveyor, and is provided with a first detector array that receives the rays emitted from the radiation source and collimated by the collimator, and
a horizontal or a transverse arm frame, one end of which is connected with an upper end of the upright arm frame, and the other end of which spans said main plate conveyor so as to be connected with the collimator, so that the upright arm frame, the horizontal or transverse arm frame, and the collimator constitute an inverted-U shaped frame, and the horizontal or transverse arm frame is provided with a second detector array that receives the rays emitted from the radiation source and collimated by the collimator.

11. The inspection system according to claim 10, further comprising protection frames that are provided at ends of said auxiliary conveyors apart from said main plate conveyor, respectively.

12. The inspection system according to claim 10, wherein said radiation source comprises an X-ray tube or an isotope radiation source.

13. The inspection system according to claim 1, wherein each of said lifting devices comprises:
a hydraulic cylinder provided under the upper platform and used to support and lift said upper platform.

14. The inspection system according to claim 1, wherein each of said lifting devices further comprises:
a leading screw transmission device comprising:
a leading screw,
a motor for driving the leading screw, and
a nut engaged with the leading screw and fixed to a bottom surface of said upper platform, so that said nut moves along the leading screw, thereby lifting said upper platform and said auxiliary conveyor, when the motor is actuated to drive the leading screw to rotate.

* * * * *